(12) United States Patent
Williams

(10) Patent No.: US 6,424,858 B1
(45) Date of Patent: Jul. 23, 2002

(54) APPARATUS AND METHOD FOR VIEWING VASCULATURE OF A HUMAN BEING

(76) Inventor: John L. Williams, 8712 W. Farm Road 124, Springfield, MO (US) 65802

( * ) Notice: Subject to any disclaimer, the term of this patent is extended or adjusted under 35 U.S.C. 154(b) by 0 days.

(21) Appl. No.: 09/190,361

(22) Filed: Nov. 12, 1998

(51) Int. Cl.$^7$ ................................................. A61B 5/00
(52) U.S. Cl. ........................ 600/473; 600/481; 250/330
(58) Field of Search ................................ 600/407, 473, 600/476, 481; 356/51; 250/226, 330, 340, 341.1, 341.3, 338.1

(56) References Cited

U.S. PATENT DOCUMENTS

| | | | |
|---|---|---|---|
| 4,767,928 A | | 8/1988 | Nelson et al. |
| 4,817,622 A | * | 4/1989 | Pennypacker et al. ...... 600/473 |
| 4,948,974 A | * | 8/1990 | Nelson et al. .............. 600/473 |
| 5,007,428 A | * | 4/1991 | Watmough .................. 600/473 |
| 5,146,923 A | | 9/1992 | Dhawan |
| 5,467,767 A | * | 11/1995 | Alfano et al. ............... 600/476 |
| 5,504,572 A | | 4/1996 | Williams et al. |
| 5,517,997 A | | 5/1996 | Fontenot |
| 5,603,328 A | * | 2/1997 | Zucker et al. .............. 250/330 |
| 5,608,210 A | * | 3/1997 | Esparza et al. ............. 600/473 |
| 5,671,738 A | * | 9/1997 | Thornberg ................... 128/897 |
| 5,801,762 A | * | 9/1998 | Dianna et al. .............. 348/357 |
| 6,032,070 A | * | 2/2000 | Flock et al. ................ 600/473 |

FOREIGN PATENT DOCUMENTS

DE      44 21 237 A1   *   12/1994

* cited by examiner

Primary Examiner—Ruth S. Smith
(74) Attorney, Agent, or Firm—Lathrop & Gage, L.C.

(57) ABSTRACT

An electronic imaging apparatus for transillumination and visually exposing vasculature of the human anatomy by passing infrared light through the portion of the anatomy to be studied and receiving infrared light which passes through the flesh and bone. By receiving only infrared light which is passed through the body, a real time image of the vasculature may be visualized as infrared light does not pass through blood filled organs, namely, veins, arteries and capillaries. A method is disclosed which describes the steps of placing the human anatomy to be studied adjacent a light source, receiving infrared light which passes through the anatomy and visualizing the resultant image of the human vasculature.

7 Claims, 3 Drawing Sheets

APPARATUS AND METHOD FOR VIEWING VASCULATURE OF A HUMAN BEING

BACKGROUND OF THE INVENTION

1. Field of the Invention

This invention relates to an innovative device and method for non-invasive, real time viewing of the veins and arteries within the human body.

2. Description of the Related Art

Generally, it is necessary to invade the human body to clearly visualize venous structures, to include veins, arteries and capillaries. It is desirable to know the physical location and positioning of certain vasculature prior to and during medical procedures such as diagnostic testing or treatment. There is no known apparatus which allows the subdural vasculature of the human body to be clearly viewed, in real time, without body invasive procedures.

It is known that to view portions of the human anatomy it is beneficial to transilluminate, or subject the anatomy to intense visible light. If the intensity of the visible light is great enough, it is possible to visualize certain portions of the subdural anatomy. Particularly, transillumination has been used to ascertain certain abnormalities, such as encephalitis, in infants. The diminutive size of the infant anatomy allows the visualization of certain such abnormalities with the use of direct transillumination, which places an intense light source opposite, or one hundred and eighty degrees from the viewing site, with the infant in between. However, such transillumination is useful only for determining general shape and structure within the body and does not facilitate visualization of specific organs or body systems. Further, the intense light needed to fully transilluminate the body is extremely hot and may be uncomfortable or painful.

Other medical devices do allow visualization of internal body structures such as Magnetic Resonance Imaging (MRI) or CAT scanning. Neither of these procedures show real time images of the internal structure, nor do they show general vasculature location or function. The use of Doppler scanning does provide some limited examination of blood flow in subdural vasculature. However, the images provided are generally poor quality and are not provided in real time. Therefore, it is difficult, if not impossible, to localize blood flow restrictions, poor circulation problems or occlusion of the arteries.

There are known devices which provide physicians with information of the location of vasculature or in identifying vasculature irregularities but which do not provide real time viewing of the vasculature, or which require surgical or laproscopic procedures. An example of such a device is found in U.S. Pat. No. 5,517,997 to Fontenot.

It is known that utilizing a narrow spectral bandwidth of visible or near visible light can, in a controlled environment, allow a visual inspection of the contents or interior of a relatively opaque object. In U.S. Pat. No. 4,767,928 to Nelson et al., a device is disclosed which utilizes collimated light which is transmitted through human flesh and received by a photo detector, whereby abnormalities within the flesh may be detected via an analog signal which is the digital result of the received light. The Nelson device is specifically used to detect abnormal or diseased flesh within the human breast and requires an analysis of digitized analog signal rather than a simple analytical visual inspection of collected light particles in a resultant image from the original transmitted light.

U.S. Pat. No. 5,146,923 to Dhawan discloses an apparatus and method for examining skin lesions with uniform light distribution and a hand held device known as a nevoscope. This apparatus does not allow visualization of significant subdural vasculature and can be used to view relatively small portions of the body, generally at or near the skin.

PRINCIPAL OBJECTS AND ADVANTAGES OF THE INVENTION

Generally, opaque objects are impervious to rays of visible light and translucent objects admit and diffuse visible light in such a manner that objects beyond the subject cannot be clearly distinguished.

The inventive device is an electronic imaging apparatus which is configured to capture an image of the interior structure of the human body, particularly the vasculature, then convert the electronic signal into a visible means which is displayed on a video monitor or is recorded for viewing. While the device can be utilized to view the vasculature of any portion of the human body, it is particularly adapted to view the vasculature of the forearm and hand.

The device provides a platform whereupon the portion of the human anatomy to be viewed is placed, and subjected to an electronic image sensor which scans the anatomical portion and then converts the image of the internal vasculature into an electronic video signal. It is necessary to shield the anatomical portion of the body to be viewed from all external visible light and therefore, the device is used in a dark room or within the confines of a curtained area.

When properly used, the inventive device provides visualization of the veins and arteries of the body part being examined and will clearly show abnormalities in the structure of the veins and arteries. Further, the device allows the user to watch blood flow in real time which may assist in diagnosing vascular disorders or diseases. The device utilizes light transfer components which alleviate the problem of heat intensity.

A principal objects and advantage of the invention is to provide an apparatus which allows a user to visualize the internal vasculature of a human being without invading the body and generally providing such an apparatus that is useful, reliable, efficient, and environmentally friendly.

It is also an object and advantage of the inventive device to allow a visual image to be obtained by passing light of a known spectral band through a translucent or opaque object.

Another object and advantage of the invention is to provide an apparatus which will allow the visualization of vasculature abnormalities during diagnostic and treatment procedures.

It is also an object and advantage of the invention to transfer the illuminative light in a manner which alleviates problems with the amount of heat generated by the light source.

It is a further object and advantage of the invention to provide a device which can record a visible two or three dimensional image of the internal structure of an opaque or translucent object by passing light of a known band width through the object.

Still another object and advantage of the invention is to provide an apparatus which allows the user to easily map the vasculature of the human body.

Yet another object and advantage of the inventive apparatus is to provide an affordable medical device which is easy to use and easy to maintain.

Other objects and advantages of the present invention will become apparent from the following description taken in conjunction with the accompanying drawings, which constitute a part of this specification and wherein are set forth exemplary embodiments of the present invention to illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
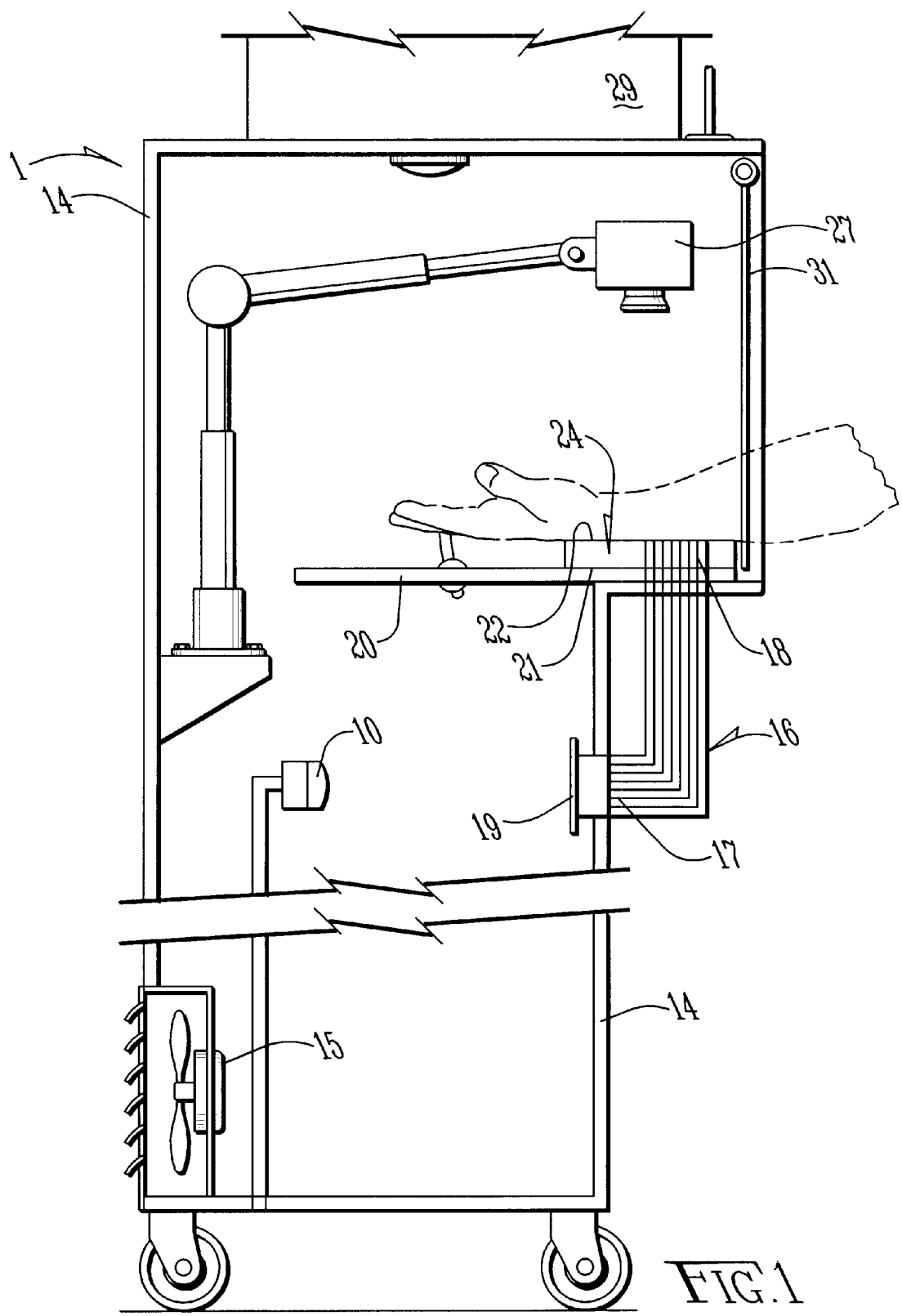
FIG. 1 is a sectional side view of one embodiment of the invention.
Figure 2:
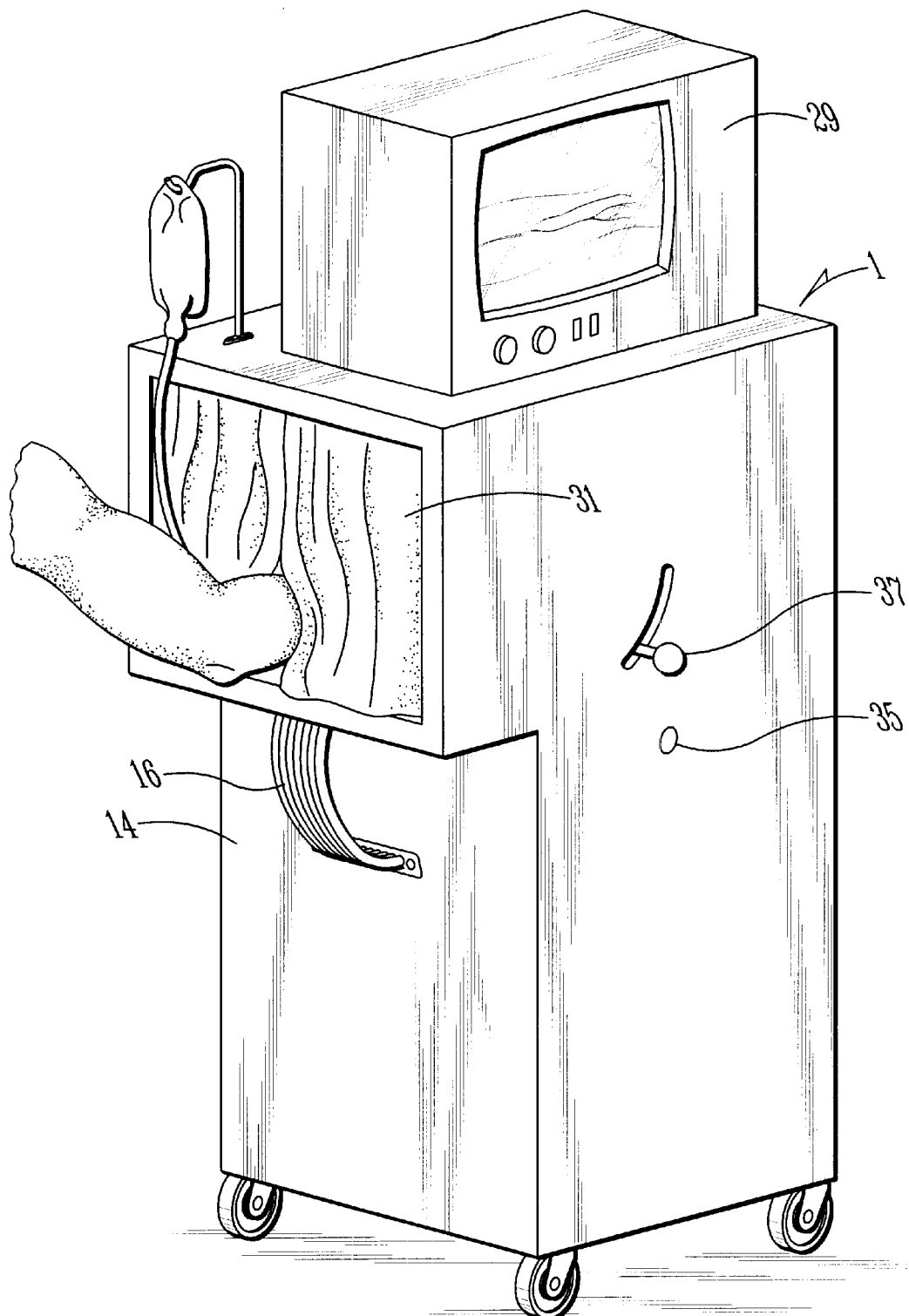
FIG. 2 is an elevation view of one embodiment of the invention.

The reference numeral 1 generally refers to an imaging apparatus in accordance with the present invention, as shown in FIGS. 1 and 2. The imaging apparatus 1 is provided with a light source 10 which may emit visible light having a predetermined emission of infrared light waves, or which may emit infrared light. The light source 10 is movably fixed within an enclosure 14. At least one mechanism for transferring light 16, having a first end 17 and a second end 18, such as a common fiber optic cable, is fixed to enclosure 14 with first end 17 maintained within enclosure 14 proximate light source 10 and positioned to operatively receive emitted light and transfer the same to second end 18. The apparatus may be provided with an optional filter 19 which may be a ultraviolet filter, a polarizing filter or a heat protection filter, or combination of these filters. Cabinet 14 may have a venting mechanism 15 such as a fan.

Fixed above enclosure 14 is a platform 20, which has a lower surface 21 and an upper surface 22, with the upper surface 22 configured to support a portion of the human anatomy such as an arm, leg or torso. Second end 18 is fixed in a predetermined position adjacent platform 20 which, in the preferred embodiment, is fitted with a translucent member 24 which allows light from second end 18 to pass through to upper surface 22.

A portion of the human anatomy is placed on upper surface 22 in a manner which allows light emitted from second end 18 to pass into and through the anatomy. Fixed a predetermined distance above upper surface 22 is a light receiving apparatus 27, such as a zero lux camera, adapted to receive low levels of infrared light. While visible light does not readily pass through the human body, except at extremely high intensity, infrared light passes through tissue and bone but not blood. Therefore, infrared light which is passed from light source 10 through the mechanism for transferring light 16 and which passes into the human body will be received by the light receiving apparatus 27. A monitor 29 is operatively connected to the light receiving apparatus 27 which allows the user to view transmitted infrared light, and the resultant image of the vasculature being examined. Due to the physical propensity of infrared light described above, the user will view a real time image of blood filled organs or systems, namely, the veins, arteries and capillaries.

It is necessary to operate the innovative imaging apparatus 1 in an environment which is dark or void of visible light between platform 20 and light receiving apparatus 27. An optional opaque curtain 31 may be drawn about platform 20 and light receiving apparatus 27. Images obtained may be archived with a recording device.

Referring to FIG. 2, a light dimmer 35 will be provided which electrically facilitates changing and controlling the intensity of light emitted. Further, a selector switch 37 allows the operator to mechanically and electrically choose between multiple provided light sources 10, which are preferably an infrared bulb and an incandescent bulb.

Platform 20 may be configured to support a specific portion of the human anatomy which is desired to be examined, such as the forearm and hand. A predetermined number of light transferring mechanism 16 facilitates adequate viewing of various portions of the anatomy. For example, seven spaced-apart light transferring mechanism 16, namely fiber optic cables, have been determined to adequately illuminate the vasculature of the forearm and hand.

Figure 3:
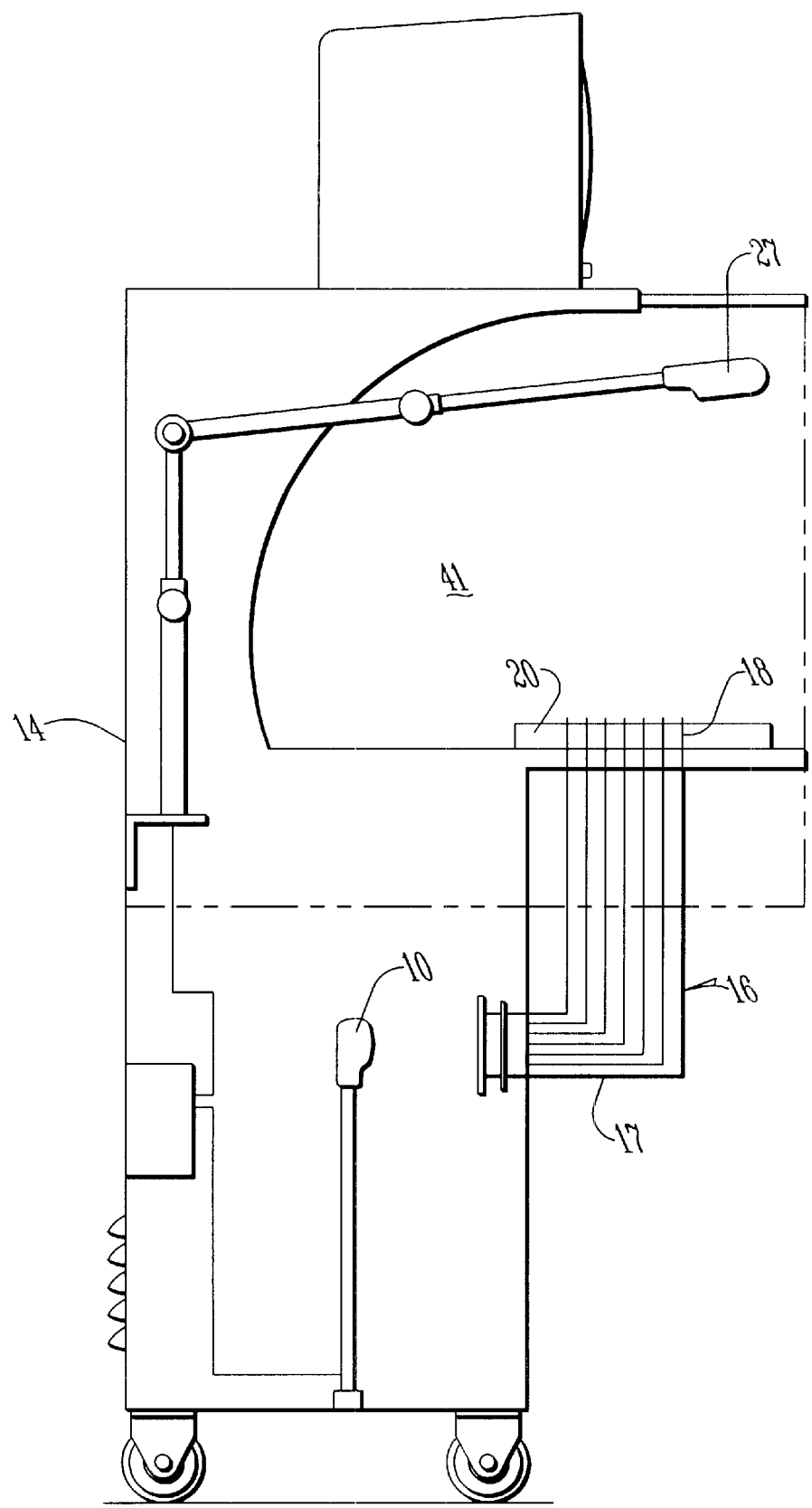
FIG. 3 is a sectional side view of another embodiment of the invention.

FIG. 3 illustrates another configuration of the innovative device wherein enclosure 14 is provided with a concave area 41 about platform 20 for easy access and maneuvering. The concave area 41 allows both the patient and the operator to comfortably work in the relatively small area.

Whereas the present invention has been described in relation to the drawings attached hereto, it should be understood that other and further modifications, apart from those shown or suggested herein, may be made within the spirit and scope of this invention.

What is claimed and desired to be covered by Letters Patent is as follows:

1. An imaging apparatus for viewing human vasculature, comprising:
   (a) an enclosure and a light emitting source within the enclosure;
   (b) a plurality of fiber optic cables having a first end and a second end, said first end proximate to said light emitting source;
   (c) a platform configured to support a portion of the human anatomy located adjacent said second end of said plurality of fiber optic cables; and
   (d) a light receiving device positioned above said platform and configured to receive infrared light emitted from said light emitting source;
   (e) a protective transmission filter fixed between the first end of the plurality of fiber optic cables and the light emitting source; and
   wherein the portion of the human anatomy supported on said platform is positioned between the second end of said plurality of fiber optic cables and said light receiving device and the light passing completely through the portion of human anatomy is received by the receiving device.

2. The imaging apparatus of claim 1 wherein the protective transmission filter is a polarization filter removably mounted between said first end of said plurality of fiber optic cables and said light emitting source.

3. The imaging apparatus of claim 1 wherein the protective transmission filter is an ultraviolet filter removably mounted between said first end of said plurality of fiber optic cables and said light emitting source.

4. The imaging apparatus of claim 1 further wherein said light emitting source further comprises at least one incandescent light source and at least one infrared light source.

5. The imaging apparatus of claim 4 further comprising a control for selectively operating said at least one incandescent light source and said at least one infrared light source.

6. The imaging apparatus of claim 1 further comprising a control for controlling the intensity of said light emitting source.

7. The imaging apparatus of claim 1 further comprising a light receiving device enclosure movably mounted about said light receiving device and said platform wherein said enclosure operatively diminishes visible light within said enclosure.

* * * * *